US005458652A

United States Patent [19]

Uebelacker

[11] Patent Number: 5,458,652

[45] Date of Patent: Oct. 17, 1995

[54] DEVICE FOR GENERATING SHOCK WAVES FOR NON CONTACT DISINTEGRATION OF CALCULI

[75] Inventor: Walter Uebelacker, Burglen, Switzerland

[73] Assignee: HMT High Medical Technologies Entwicklungs-und Vertriebs AG, Kreuzlingen, Switzerland

[21] Appl. No.: 221,278

[22] Filed: Mar. 31, 1994

Related U.S. Application Data

[63] Continuation of Ser. No. 17,229, Feb. 12, 1993, abandoned.

[30] Foreign Application Priority Data

Sep. 28, 1992 [EP] European Pat. Off. .............. 92116582

[51] Int. Cl.$^{6}$ ........................................ A61B 17/22

[52] U.S. Cl. ........................................ 601/4; 367/147

[58] Field of Search .................................... 606/127, 128; 601/3, 4; 367/147; 128/24 A, 24 EL

[56] References Cited

U.S. PATENT DOCUMENTS

| | | | |
|---|---|---|---|
| 4,715,376 | 12/1987 | Nowaiki et al. | 128/24 EL |
| 4,809,682 | 3/1989 | Folssmann et al. | 128/24 EL |
| 4,938,781 | 7/1990 | Pimiskern | 128/24 EL |
| 5,146,912 | 9/1992 | Eizenhoefer | 128/24 EL |
| 5,195,508 | 3/1993 | Muller et al. | 128/24 EL |
| 5,251,614 | 10/1993 | Cathignol et al. | 128/24 EL |

FOREIGN PATENT DOCUMENTS

| | | | |
|---|---|---|---|
| 0362529 | 4/1990 | European Pat. Off. | 601/4 |
| 2635635 | 2/1978 | Germany . | |
| 3844419 | 7/1989 | Germany | 128/24 EL |
| 1227185 | 4/1986 | U.S.S.R. | 128/24 EL |
| 9110403 | 7/1991 | WIPO | 128/24 EL |

*Primary Examiner*—Stephen C. Pellegrino
*Assistant Examiner*—Glen Dawson
*Attorney, Agent, or Firm*—Jordan and Hamburg

[57] ABSTRACT

The invention relates to a device for generating shock waves by means of a spark gap by using two electrodes. At a spark gap, apart from the desired shock waves, low frequency sound parts are generated. These sound parts have a disturbing effect during therapy. According to the invention, for the reduction of the low frequency sound parts it is provided to arrange the electrodes in a pressure-tight tube surrounding them.

5 Claims, 1 Drawing Sheet

DEVICE FOR GENERATING SHOCK WAVES FOR NON CONTACT DISINTEGRATION OF CALCULI

This application is a continuation, of application Ser. No. 08/017,229, filed Feb. 12, 1993, now abandoned.

The invention pertains to a device for fragmenting calculi.

BACKGROUND OF THE INVENTION

A similar device is known from DE-PS 2635 635. The electrical discharge occurs in between the electrodes, which are placed in liquid and in the first focus of an ellipsoid. After the electrical discharge, because of the explosive evaporation of the liquid, a shock wave is propagated and is focused into the second focus of the ellipsoid. The calculi to be disintegrated are placed in this second focus. In addition to the shock wave, low frequency parts are emitted by the cavitation bubble. The low frequency sound waves which are placed in the audible region are disturbing for a patient as well as for personnel, because of their high amplitude. Additionally, these low frequency waves induce pain during therapy.

The usage of an electrolyte as a liquid medium which surrounds the electrodes is also known.

SUMMARY OF THE INVENTION

The device of the present invention overcomes the drawbacks of the prior art by damping the low frequency parts after shock wave generation.

A reduction of low frequency parts is obtained by using a tube that surrounds the electrodes. The shock wave which is generated by the discharge, is able to penetrate the tube, and is then transmitted by the surrounding liquid. On the other hand the maximum gas bubble radius is reduced because of the suppressed expansion of the gas bubble. This leads to a decreased sound generation. The noise stress of the patient and the personnel is clearly decreased, without decrease of the efficiency of stone disintegration. Furthermore a relatively painless treatment is possible.

DETAILED DESCRIPTION OF THE PREFERRED EMBODIMENT

Figure 1:
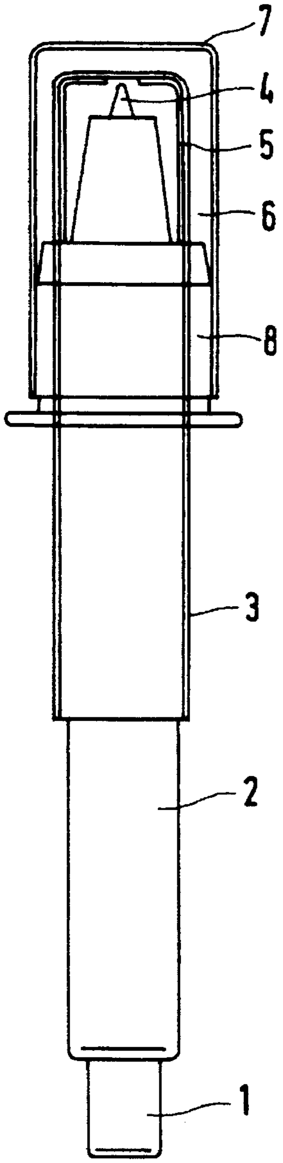
FIG. 1 is a schematic side view of the device of the present invention.

The electrodes 4 and 5 are placed in the tube 7. The tube 7, that is closed at the upper side, is connected pressure tight to the device. The tube 7 contains a liquid medium 6 which surrounds the electrodes 4 and 5. The conductivity of the liquid medium 6 is preferably 100 uS to 100 mS.

The thickness of the tube 7 is smaller than the wave length of the shock wave, so that the shock wave will not be reflected by the inside of the tube. When the tube 7 is metal, a preferred thickness of the wall of the tube 7 is 0.1–0.6 mm. By using plastics, whereby it has the same acoustic impedance like the liquid media 6, the thickness of this tube may be thicker. The thickness of the wall of tube 7 is preferably 1 to 10 mm, when the tube 7 is plastic.

The electrode 5 is insulated, except for the area around the electrode 4, and is perpendicular to electrode 4. Thus the electrical discharge spatially alternates at the non insulated area of the electrode 5, which leads to an increasing volume of disintegration at the second focus of the eillipsoid.

According to FIG. 1, the inner conductor 1 is connected to electrode 4, and the outer conductor 3 is connected to electrode 5. The tube 7 is connected to the device either by being fixed to the insulator 8, or by being screwed to it.

Figure 2:
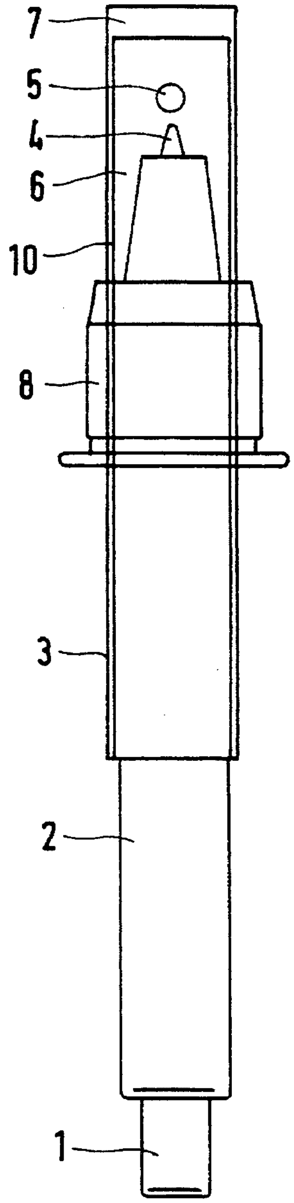
FIG. 2 is a device of the present invention in a view that is related to FIG. 1.

In the configuration shown in FIG. 2 the tube forms the outer conductor 3 and the electrode 5 is electrically connected to the tube 7. To prevent partial discharge at the inner wall of the tube, the inner wall is electrically insulated from the electrode 4 by the insulator 10.

Figure 3:
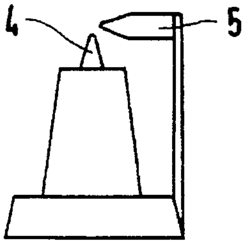
FIG. 3 a part of the electrode of a device in schematic side view.

Good disintegration results are achieved with an electrode arrangement shown in FIG. 3. Like in FIG. 1 the electrode symmetric axes are perpendicular and the electrode 5 is bent like a "L".

An explanation of the operation of the device of the present invention follows. At the point of time of the electrical discharge between the electrodes 4 and 5 the liquid media is evaporated explosively and strongly heated. The generated plasma drives a shock wave in front of it, till the propagation velocity of the plasma is smaller than the propagation velocity of sound in water, then a shock wave detaches quasi spherical from the plasma.

If the wall has the correct dimension, the shock wave is able to penetrate the wall.

The cavitation bubble which is generated by the electrical discharge, expands and increases the pressure in the tube, till a volume is reached that correlates to the temperature and volume of the gas bubble. Afterwards the gas bubble collapses again.

Because of the increased pressure in the tube, the maximum gas bubble radius is limited. This leads to a reduction of sound generation of the gas bubble.

What is claimed is:

1. A device for generating shock waves for non-contact disintegration of calculi comprising a first and a second electrode; a pressure-tight tube encasing said first and second electrodes for limiting a radius of a gas bubble produced by an electrical discharge between said first and second electrodes thereby reducing sound generated in an audible region and pain experienced by a patient, said tube is a metal tube electrically connected to at least one of said first and second electrodes, and said tube operates as an outer conductor; and a liquid medium in said tube, said liquid medium being evaporated explosively during electrical discharge between said first and second electrodes, thereby generating a shockwave capable of disintegrating calculi.

2. The device of claim 1, wherein a thickness of a wall of the tube is between 0.1 and 0.6 mm.

3. The device of claim 1, wherein at least one of the electrodes is L-shaped.

4. The device of claim 1, wherein the liquid medium in the tube has a conductivity of 100 uS to 100 mS.

5. The device of claim 1, wherein one of said first and second electrodes is insulated.

* * * * *